United States Patent
Chuang et al.

(10) Patent No.: US 10,705,077 B2
(45) Date of Patent: Jul. 7, 2020

(54) METHOD FOR DETECTING ANALYTE CONCENTRATION

(71) Applicant: NATIONAL CHENG KUNG UNIVERSITY, Tainan (TW)

(72) Inventors: Han-Sheng Chuang, Tainan (TW); Wei-Long Chen, Tainan (TW)

(73) Assignee: NATIONAL CHENG KUNG UNIVERSITY, Tainan (TW)

( * ) Notice: Subject to any disclaimer, the term of this patent is extended or adjusted under 35 U.S.C. 154(b) by 308 days.

(21) Appl. No.: 15/826,712

(22) Filed: Nov. 30, 2017

(65) Prior Publication Data

US 2019/0033304 A1    Jan. 31, 2019

(30) Foreign Application Priority Data

Jul. 26, 2017    (TW) .................................. 106125166

(51) Int. Cl.
| | | |
|---|---|---|
| *G01N 33/543* | (2006.01) | |
| *G01N 25/18* | (2006.01) | |
| *G01N 33/68* | (2006.01) | |
| *G01N 33/533* | (2006.01) | |

(52) U.S. Cl.
CPC ....... *G01N 33/54306* (2013.01); *G01N 25/18* (2013.01); *G01N 33/54346* (2013.01); *G01N 33/533* (2013.01); *G01N 33/6863* (2013.01); *G01N 2333/525* (2013.01); *G01N 2458/00* (2013.01)

(58) Field of Classification Search
None
See application file for complete search history.

(56) References Cited

U.S. PATENT DOCUMENTS

| | | | |
|---|---|---|---|
| 4,407,964 A | 10/1983 | Elings et al. | |
| 5,941,821 A * | 8/1999 | Chou | A61B 5/0095 600/316 |
| 6,361,956 B1 * | 3/2002 | Hanninen | G01N 33/54326 250/298 |
| 6,551,788 B1 * | 4/2003 | Bell | G01N 33/54313 435/7.1 |
| 2011/0097723 A1 * | 4/2011 | Liu | B82Y 15/00 435/6.1 |
| 2013/0224763 A1 | 8/2013 | Kimura | |

FOREIGN PATENT DOCUMENTS

| | | |
|---|---|---|
| CN | 101988922 A | 3/2011 |
| TW | I351519 B | 11/2011 |
| TW | 201725375 A | 7/2017 |

OTHER PUBLICATIONS

Xiaohua Huang et al., "Gold nanoparticles: Optical properties and implementations in cancer diagnosis and photothermal therapy," Journal of Advanced Research, vol. 1, Issue 1, Jan. 2010, pp. 13-28.

* cited by examiner

*Primary Examiner* — Gary Counts
(74) *Attorney, Agent, or Firm* — CKC & Partners Co., LLC

(57) ABSTRACT

A method for detecting an analyte concentration of the present invention includes performing a competitive reaction between a first complex and an analyte standard or an analyte sample, so that the first complex may combine with a metal nanoparticle, and a second complex of a control group and a third complex of a sample group are respectively formed. Then, a difference of heat diffusivity of the second complex and the third complex may determine an analyte sample concentration of the sample group is higher or lower than a pre-determined analyte standard concentration of the control group.

14 Claims, 14 Drawing Sheets

METHOD FOR DETECTING ANALYTE CONCENTRATION

RELATED APPLICATIONS

This application claims priority to Taiwan Application Serial Number 106125166, filed Jul. 26, 2017, which is herein incorporated by reference.

BACKGROUND

Field of Invention

The present invention relates to a method for detecting analyte concentration. More particularly, the present invention relates to a method using a dichotomy method and a heat diffusivity of particles in a solution to determine whether the analyte concentration is higher or lower than a standard concentration.

Description of Related Art

With the progress of the medical science, the development of a non-invasive detection method for a disease screening becomes more and more important. For example, a common non-invasive detection method for the diabetic retinopathy is ocular optical coherence tomography (OCT). However, both the apparatus and the fee for the examination are expensive. Another detection method is fluorescence angiography, while it is an invasive method since a fluorescent dye has to be injected into veins. According to the problems, it is necessary to develop a quick screening, low costs, and non-invasive detection method.

One method is provided. An antigen standard is labelled with a fluorescent marker, and an antibody corresponding to the antigen standard then binds to a carrier (hereinafter as antibody carrier). Next, an antigen sample, the antigen standard and the antibody carrier are mixed to perform a competition reaction between the antigen sample and the antigen standard, and one of the antigen sample and the antigen standard will bind to the antibody carrier. Afterwards, the fluorescent marker on the antigen standard is detected to observe Brownian motion of the antigen standard. The more the free-form antigen standard is, the higher concentration of the antigen sample is, and thus the concentration may be obtained. However, since the antigen sample and the antigen standard are mixed together, the antigen standard can't be repeatedly used to perform several groups of detection, thus the costs increase. Besides, the sample is likely to be polluted in this method.

The other method is also provided. First particles having at least two particle sizes and a specific ratio of the at least two particle sizes are applied to increase the detection dynamic range, in which the first particles bind to a first binding ligand corresponding to an analyte sample, Specifically, a large first particle, a small first particle, and a second particle having a marker and a second binding ligand which can bind with the first binding ligand, are simultaneously added into a sample solution having the analyte sample. Next, a competition reaction is performed between the second particle and the analyte sample, so as to bind with the large first particle and the small first particle. The concentration of the analyte sample is determined by the signal intensity of the bound large/small first particle. However, at least three types of particles have to be added into the analyte sample, and this substantially increases the complexity of detection. Besides, the limitation of the particle size of the large first particle and the small first particle is highly strict, leading to limited applicable field of the method.

Another method is provided. A hybrid antibody is formed by binding an antibody onto a surface of a nanoparticle. Then, the hybrid antibody is added to a sample solution containing an antigen. Next, a difference of Brownian motion is detected after the antigen binds to the hybrid antibody in the sample solution, and a concentration of the antigen is calculated by a calibration curve obtained from a reference standard beforehand. However, the method requires the calibration curve, and when the concentration of the sample solution is not in the range of the calibration curve, or when the sample solution is changed to other sample solutions having different antigens, more preparations are required to detect the analyte concentration in the sample solution. And the method is also limited by the lowest detectable concentration (i.e. poor detection sensitivity). Therefore, the method is not suitable for quick disease screening. Moreover, in order to increase the difference in the volume of the hybrid antibody (which affects the difference of Brownian motion) by binding the antibody to the nanoparticle, a particle size of the nanoparticle is small, leading to problems such as manufacturing complexity or small detectable dynamic range.

Therefore, it is necessary to provide a method for detecting an analyte concentration. The method has good sensitivity, low detection limit, a wide dynamic range, and the method is also easy to operate, rapid and has good reproducibility, so as to tackle the problems described above.

SUMMARY

An aspect of the present invention provides a method for detecting an analyte concentration. In one embodiment, the method includes the following steps. First, at least two reaction solutions are provided. Each of the reaction solutions includes a first complex, and the first complex includes a labeling particle, a binding ligand fixed on a surface of the labeling particle, and a substrate binding to the binding ligand. Next, an analyte standard and metal nanoparticles are simultaneously added into one of the reaction solutions, so as to form a second complex. Each of the metal nanoparticles has the binding ligand, and the analyte standard in the one of the reaction solutions has a known concentration. Then, a sample including an analyte sample and the metal nanoparticles are simultaneously added into the other one of the reaction solutions, so as to form a third complex. The analyte sample in the other reaction solution has an unknown concentration, an equivalent particle size of the labeling particle is greater than an equivalent particle size of each of the metal nanoparticles, and the substrate, the analyte standard and the analyte sample are substantially the same. Then, a first heat diffusivity of the second complex and a second heat diffusivity of the third complex are detected using a light source. Afterwards, an analyte concentration determination step is performed, in which when the first heat diffusivity is less than the second heat diffusivity, the unknown concentration is higher than the known concentration; or, when the first heat diffusivity is greater than the second heat diffusivity, the unknown concentration is lower than the known concentration.

According to an embodiment of the present invention, detecting the first heat diffusivity and the second heat diffusivity using the light source may further includes applying a laser to the metal nanoparticles.

According to an embodiment of the present invention, the equivalent particle size of each of the metal nanoparticles is not greater than 80 nanometers (nm).

According to an embodiment of the present invention, an equivalent particle size of the labeling particle is equal to or greater than 100 nm.

According to an embodiment of the present invention, a ratio of the equivalent particle sizes of the labeling particle to one of the metal nanoparticles may be 2.5 to 125.

According to an embodiment of the present invention, a material of the metal nanoparticles includes gold.

According to an embodiment of the present invention, a material of the labeling particle includes a fluorescent compound.

According to an embodiment of the present invention, a power of the laser is not greater than 0.23 mW.

According to an embodiment of the present invention, the sample includes tear, blood, urine, serum or other biological samples.

According to an embodiment of the present invention, the unknown concentration is equal to or greater than 10 pg/ml.

According to an embodiment of the present invention, the light source excites the respective labeling particles of the second complex and the third complex.

According to an embodiment of the present invention, the light source includes a mercury lamp, a xenon lamp, or a metal halide lamp.

According to an embodiment of the present invention, the binding ligand includes an antigen, an antibody, a receptor or a ligand.

According to an embodiment of the present invention, the substrate, the analyte standard and the analyte sample respectively include an antibody of the antigen of the binding ligand, an antigen of the antibody of the binding ligand, a ligand of the receptor of the binding ligand, or a receptor of the ligand of the binding ligand.

The detection sensitivity and a dynamic range increase, and detection limit decreases in the method for detecting the analyte concentration of the present invention. Furthermore, the method is easy to operate and has good reproducibility. The method for detecting the analyte concentration may be applied to a non-invasive disease screening.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
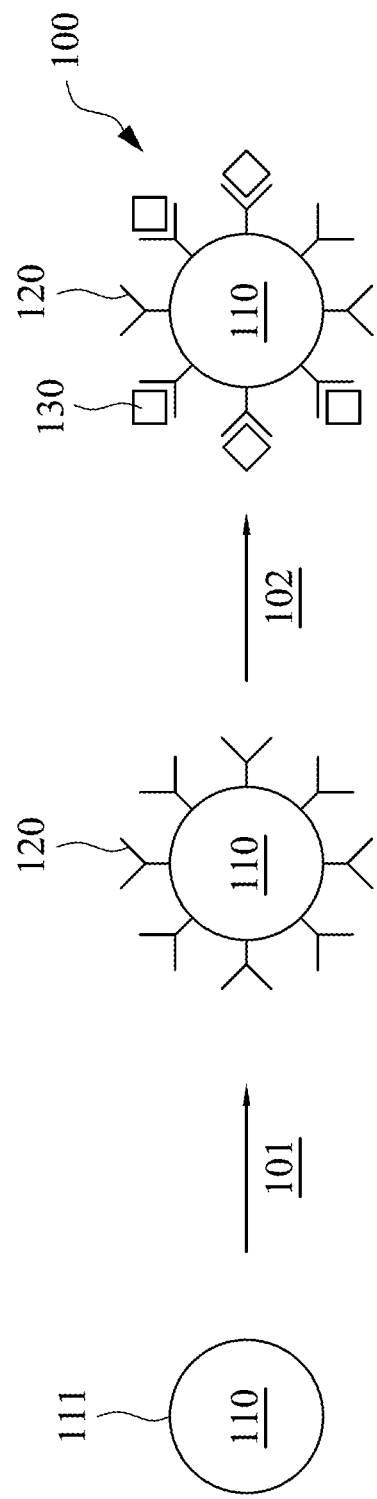
FIG. 1 is a flow chart of forming a first complex according to some embodiments of a method for detecting an analyte concentration of the present invention.

A method for detecting an analyte concentration of the present invention includes performing a competition reaction between a first complex and an analyte sample (or an analyte standard) to bind with metal nanoparticles. A second complex of a control group or a third complex of a sample group is formed when the metal nanoparticles bind to the first complex. Based on a difference between heat diffusivities of the second complex and the third complex, a concentration of the analyte sample of the sample group may be determined whether it is higher or lower than the analyte standard concentration of the control group.

Further, the difference between the heat diffusivities of the second complex and the third complex is resulted from the analyte sample concentration. When the analyte sample concentration is high, a reaction between the metal nanoparticles and the analyte sample is more significant than a reaction between the metal nanoparticles and the first complex. Therefore, a formed complex has less metal nanoparticles binding thereto. On the other hand, when the analyte sample concentration is low, the reaction between the metal nanoparticles and the first complex is more significant than the reaction between the metal nanoparticles and the analyte sample. Therefore, the formed complex has more nanoparticles binding thereto, leading to increase of a volume of the formed complex and reduction of the heat diffusivity of the formed complex. In addition, the method of the present invention further triggers a surface plasmon resonance of the metal nanoparticles on the second complex and the third complex by using a laser, in which the surface plasmon resonance enhances a heat diffusion effect, thereby increasing detection sensitivity. Accordingly, the method for detecting the analyte concentration of the present invention has advantages of high detection sensitivity, low detection limit, a wide dynamic range, being easy to operate and good reproducibility. Furthermore, the method may be applied to a non-invasive and quick disease screening.

The binding ligand in the specification of the present invention refers to a substance having a specific binding affinity to a specific analyte. For example, an antibody and an antigen, a protein and its receptor or other substances with a similar relationship may be the binding ligand of each other.

The heat diffusivity in the specification of the present invention refers to a speed of Brownian motion (i.e. a degree of diffusion) of the specific analyte, in which the speed of Brownian motion is detected by a light source for excitation. The larger the volume of the substance is, the less significant Brownian motion is, and hereinafter as less heat diffusivity.

The dichotomy method in the specification of the present invention refers to a method including defining a default concentration (or a standard concentration) first, so as to determine whether the unknown concentration is higher or lower than the default concentration by comparing the heat diffusivity difference. The method does not require a calibration curve to perform quantification and determine an actual value of the analyte concentration, and thus the method of the present invention may effectively decrease the detection limit, increase the detection sensitivity and reduce the detection time.

The high concentration in the specification of the present invention refers to the analyte sample concentration higher than the concentration of the control group; inversely, the low concentration refers to the analyte sample concentration lower than the concentration of the control group.

The equivalent particle size of each of the metal nanoparticles of the present invention in the specification refers to a size of each of the metal nanoparticles that is not bound with the binding ligand.

A various steps of the method for detecting the analyte concentration of the present invention are described as follows.

1. Providing at least Two Reaction Solutions

The reaction solution of the present invention includes a first complex. One of the provided reaction solutions is used to form the second complex of the control group, and the other one of the provided reaction solutions is used to form the third complex of the sample group. That is, the method of the present invention may detect several sample groups simultaneously. The detailed will be described later.

FIG. 1 is incorporated to describe steps of forming a first complex 100. FIG. 1 is a flow chart of forming a first complex 100 according to one embodiment of a method for detecting an analyte concentration of the present invention. First, as shown in step 101, a binding ligand 120 is fixed on a surface 111 of a labeling particle 110, in which the surface 111 of the labeling particle 110 may be modified with an amine group. An antibody is used as the binding ligand 120 in FIG. 1, while other substances may also be used as the binding ligand. The method of fixing the binding ligand 120 may be, for example, forming a covalent bond between the binding ligand 120 and the labeling particle 110. The covalent bond may be, for example, an amide bond formed by carbodiimide crosslinker chemistry.

Next, as shown in step 102, the binding ligand 120 fixed on the surface 111 of the labeling particle 110 reacts with a substrate 130, thereby forming the first complex 100. An amount of the substrate 130 attached to the binding ligand 120 depends on the reaction time. The reaction time of the present invention is not limited, while it's preferable to use a same reaction time in the same experiment.

As shown in FIG. 1, the first complex 100 includes the labeling particle 110, the binding ligand 120 fixed on the surface 111 of the labeling particle 110, and the substrate 130 binding to the binding ligand 120. The first complex 100 substantially disperses in a saline solution, so as to form the reaction solutions (not shown).

In one embodiment, a material of the labeling particle 110 may include a fluorescent compound. In one example, the surface 111 of the labeling particle 110 may be modified with an amine group. In one example, an equivalent particle size of the labeling particle 110 may be equal to or greater than 100 nanometers (nm). It is noted that a combination of the competition reaction and the dichotomy method increases the detection sensitivity, and the metal nanoparticles increase the heat diffusivity difference in the present invention. Accordingly, the labeling particle 110 having greater equivalent particle size may be used, in which the labeling particle 110 having greater equivalent particle size is relatively easy to obtain and has a stable characteristic, and a wider dynamic range may be provided. Therefore, the present invention has advantages of good reproducibility, a widely detectable concentration range, low costs and being easy to operate.

In one embodiment, the binding ligand 120 may include but is not limited to an antigen, an antibody, a receptor or a ligand.

In one embodiment, the substrate 130 may include but is not limited to an antibody of the antigen of the binding ligand 120, an antigen of the antibody of the binding ligand 120, a ligand of the receptor of the binding ligand 120, or a receptor of the ligand of the binding ligand 120. In one embodiment, a reference standard of the analyte sample (i.e. the analyte standard) may be used as the substrate 130 of the first complex 100. In other words, the substrate 130, the analyte sample and the analyte standard are all same.

In one embodiment, the reaction solutions may be a buffer solution commonly used when performing various protein reactions. For example, but is not limited to: phosphate buffered saline (PBS), phosphate buffered saline tween 20 (PBST), tris buffer saline (TBS) or the like.

2. Forming a Second Complex of a Control Group

Figure 2:
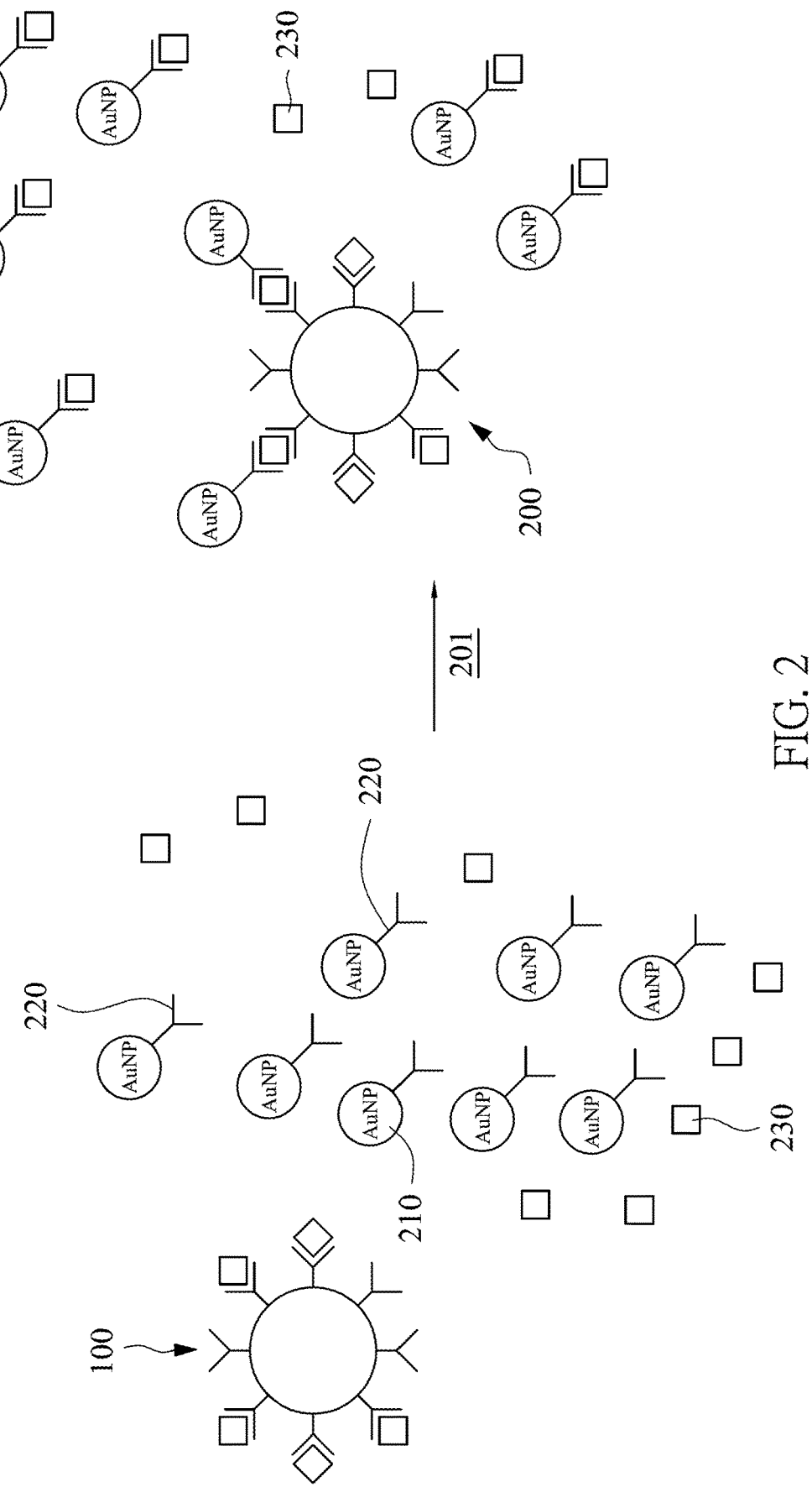
FIG. 2 is flow chart of forming a second complex according to one embodiment of a method for detecting an analyte concentration of the present invention.

FIG. 2 is incorporated to describe the flow of forming the second complex of the control group. FIG. 2 is flow chart of forming a second complex 200 according to one embodiment of a method for detecting an analyte concentration of the present invention. As shown in a step 201 of FIG. 2, metal nanoparticles 210 and an analyte standard 230 are simultaneously added into the reaction solution, in which each of the metal nanoparticles 210 has one binding ligand 220. A competition reaction is performed between the analyte standard 230 and the first complex 100 of FIG. 1, so as to form the second complex 200 including the first complex 100 and the metal nanoparticles 210, in which the analyte standard 230 has a known concentration in the reaction solution. In one embodiment, the equivalent particle size of the labeling particle 110 (FIG. 1) is greater than the equivalent particle size of each of the metal nanoparticles 210. The known concentration may be adjusted depending on the analyte sample, and the present invention is not limited to any specific example.

It is noted that when the metal nanoparticles 210 and the analyte standard 230 are not added into the reaction solution at the same time, for example, when the metal nanoparticles 210 react with the analyte standard 230 before added, the competition reaction does not occur, and the analyte sample concentration can't be detected.

In some embodiments, before the step 201 is performed, the method of the present invention further includes modifying the binding ligand 220 onto each of the metal nanoparticles 210. The modifying step may be performed by any chemical modification method using a kit product and any common modification method, and the present invention is not limited to any specific example.

The formed second complex 200 may be the control group of the method for detecting the analyte concentration of the present invention. The heat diffusivity of the second complex 200 in the reaction solution is used as a standard line to determine whether the heat diffusivity of the third complex 300 formed later is greater or less than the heat diffusivity of the second complex 200. Therefore, the concentration of the analyte sample may be determined.

3. Forming a Third Complex of a Sample Group

Figure 3A:
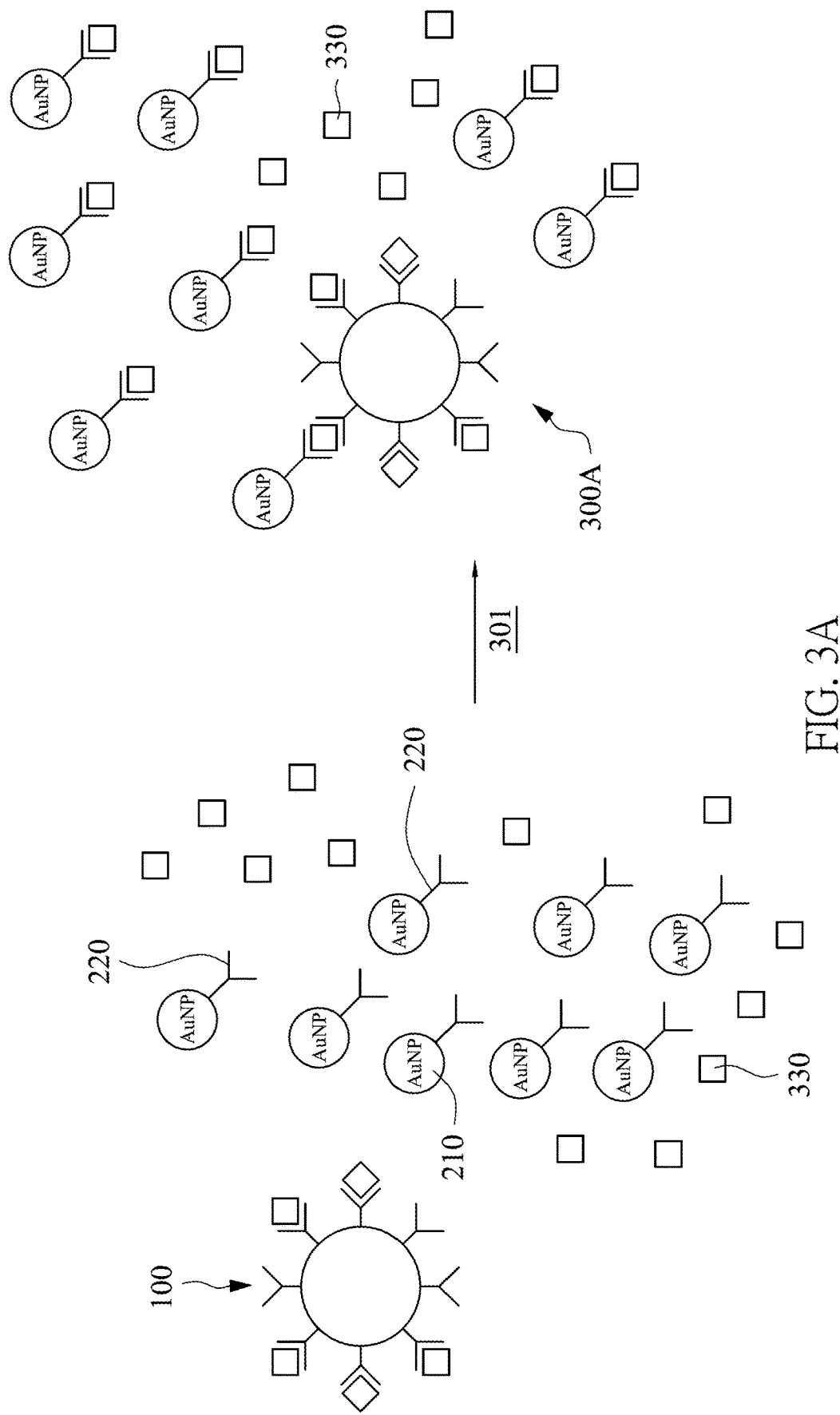
FIG. 3A is a view of forming a third complex 300A.
Figure 3B:
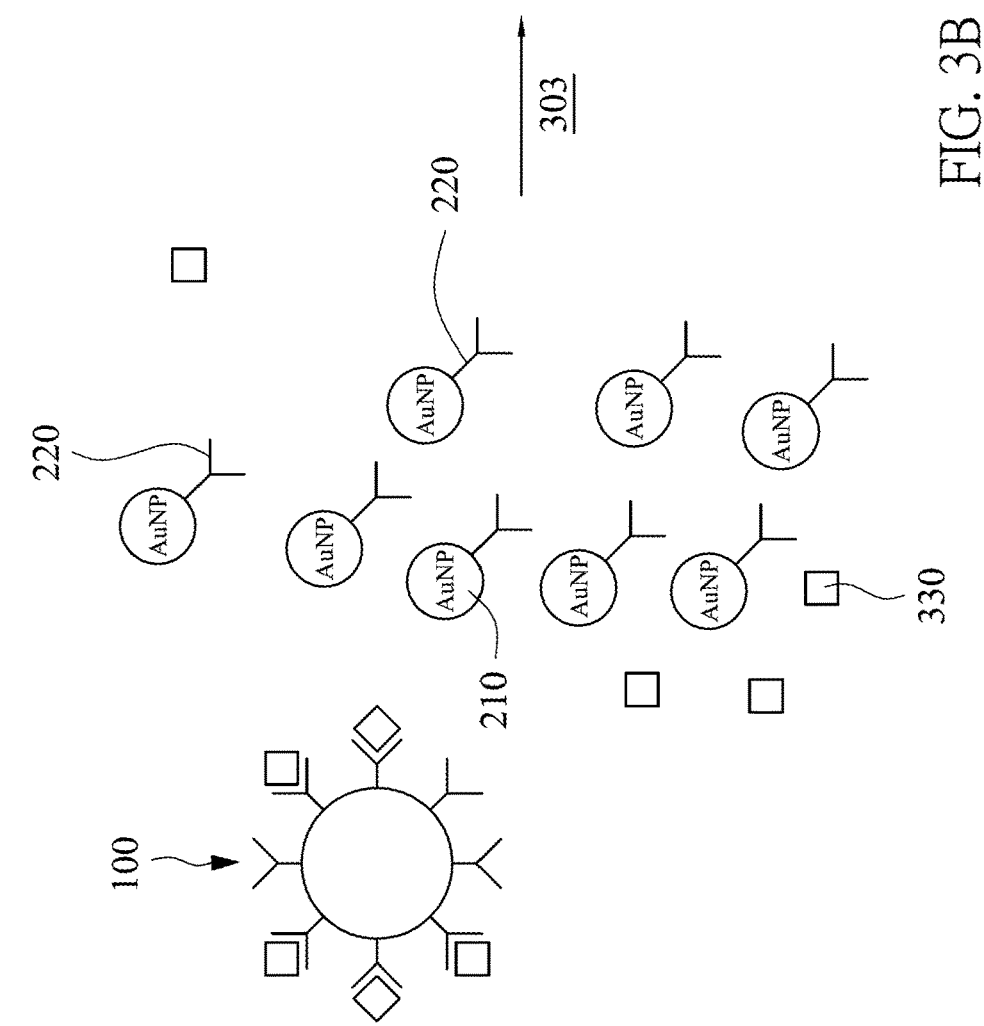
FIG. 3B is a view of forming a third complex 300B.

FIG. 3A and FIG. 3B are incorporated to describe the situations where a concentration of an analyte sample 330 is higher or lower than the concentration of the analyte standard 230 of FIG. 2. Referring to FIG. 3A, FIG. 3A is a view of forming a third complex 300A, in which the analyte sample 330 has a concentration higher than the analyte standard 230. As shown in a step 301 of FIG. 3A, the metal nanoparticles 210 and a sample including the analyte sample 330 are simultaneously added into the other reaction solution. The metal nanoparticles 210 are same as that of FIG. 2, in which each of the metal nanoparticles 210 has the binding ligand 220 and the metal nanoparticles have an equal amount as that mentioned in FIG. 2. The competition reaction is performed between the analyte sample 330 and the first complex 100 of FIG. 1, so as to form the third complex 300A including the first complex 100 and the metal nanoparticles 210.

As shown in FIG. 3A, because the analyte sample 330 has the higher concentration, a reaction between the analyte sample 330 and the metal nanoparticles 210 is more significant than a reaction between the metal nanoparticles 210 and the first complex 100. Accordingly, most of the nanoparticles 210 bind to the analyte sample 330, and few nanoparticles 210 bind to the first complex 100, thereby forming the third complex 300A having a smaller volume than the second complex 200 of FIG. 2.

Next, referring to FIG. 3B, FIG. 3B is a view of forming a third complex 300B, in which the analyte sample 330 has a concentration lower than the analyte standard 230. A step 303 of FIG. 3B is same as the step 301 of FIG. 3A. As shown in FIG. 3B, because the analyte sample 330 has the lower concentration, the reaction between the metal nanoparticles 210 and the first complex 100 is more significant than the reaction between the analyte sample 330 and the metal nanoparticles 210. Accordingly, a portion of the metal nanoparticles 210 bind to the first complex 100, thereby forming the third complex 300B having a larger volume than the second complex 200 of FIG. 2.

In one embodiment, the concentration (corresponding to the detection limit of the method of the present invention) of the analyte sample 330 may be equal to or greater than 10 pg/ml.

In one embodiment, each of the metal nanoparticles 210 may have the equivalent particle size not more than 80 nm. In other embodiment, a material of the metal nanoparticles 210 includes gold.

In one embodiment, a ratio of the equivalent particle sizes of the labeling particle 110 to one of the metal nanoparticles 210 may be, for example, 2.5 to 125, while the present invention is not limited to the specific range. Any ratio may be chosen as long as the complex formed by the labeling particle 110 and the metal nanoparticles 210 has different heat diffusivity according to different amount of the metal nanoparticles 210 binding to the labeling particle 110. However, it is noted that the greater the equivalent particle size of the labeling particle 110 is, the poorer the sensitivity is. Therefore, in one embodiment, the equivalent particle size of the labeling particle is in a range of 100 nm to 5 micrometers (μm).

In one embodiment, the binding ligand 220 may include but is not limited to an antigen, an antibody, a receptor or a ligand. The binding ligand 220 may be same as or different from the binding ligand 120 of FIG. 1. In one embodiment, the analyte standard 230 and the analyte sample 330 are substantially same as the substrate 130, and may not be repeated herein.

In one embodiment, the sample including the analyte sample 330 may include tear, blood, urine, serum or other biological samples.

Specifically, a pair which can affinity, covalently, ionically, physically or chemically bind to each other may be used as the analyte standard (or analyte sample) and its the binding ligand of the present invention.

4. Detecting Heat Diffusivities of the Second Complex and the Third Complex

Next, the heat diffusivities of the second complex and the third complex are detected using a light source. Specifically, the step of detecting the heat diffusivities is mainly performed by using the light source to excite the respective labeling particles of the second complex and the third complex, so as to observe Brownian motion in the respective reaction solutions. In one embodiment, the light source may be, for example, a mercury lamp, a xenon lamp, or a metal halide lamp.

In one embodiment, the method of the present invention further includes applying a laser to the metal nanoparticles 210 of the second complex and the third complex when the second complex and the third complex are exposed to the light source. In one example, a power of the laser is not greater than 0.23 mW. When the power of the laser is too great, excessive energy may affect the binding between the analyte and the binding ligand, or structures of the analyte or the binding ligand itself. In other examples, a wavelength of the laser may be in a range of a wavelength of visible light, e.g. a green light laser.

5. Performing an Analyte Concentration Determination Step

The analyte concentration determination step refers to comparing a heat diffusivity difference between the second complex and the third complex.

FIG. 2, FIG. 3A and FIG. 3B are incorporated to describe where the heat diffusivity difference between the second complex and the third complex comes from.

As the step of forming the third complex described above, when the analyte sample 330 has the concentration higher than the analyte standard 230, the third complex 300A has the volume smaller than the second complex 200. Therefore, the heat diffusivity of the third complex 300A is greater than the heat diffusivity of the second complex 200 (i.e. Brownian motion of the third complex 300A is more significant). In other words, when the third complex has the heat diffusivity greater than the second complex of the control group, the analyte sample in the sample group has the concentration higher than the analyte standard of the control group.

On the other hand, when the analyte sample 330 has the concentration lower than the analyte standard 230, the third complex 300B has the volume larger than the second complex 200. Therefore, the heat diffusivity of the third complex 300B is less than the heat diffusivity of the second complex 200 (i.e. Brownian motion of the third complex 300B is less significant). In other words, when the third complex has the heat diffusivity less than the second complex of the control group, the analyte sample in the sample group has the concentration lower than the analyte standard of the control group.

It is understood that though only one first complex, one second complex and one third complex are shown in FIG. 1, FIG. 2, FIG. 3A and FIG. 3B for simplification of the figures, plural first complexes, plural second complexes and plural third complexes may be used practically.

The following provides a various examples to describe the method for detecting the analyte concentration and the advantages thereof.

EXAMPLE 1

Preparing Reaction Solution including a First Complex

2 μl of the labeling particle (concentration: $4.54 \times 10^{12}$ particles/ml) were washed by 2-(N-morpholino) ethanesulfonic acid (MES), in which the labeling particle was a polystyrene fluorescent particle (diameter: 200 nm; product NO.: 8764; provided by Thermo Fisher) modified by an amine group, and the fluorescent particle had yellow-green fluorescent with an emission wavelength of 515 nm. Then, 4 μl of N-hydroxysuccinimide (NHS; concentration: 10 μg/μl), 2 μl of 1-ethyl-3-(3-dimethylaminopropyl) carbodiimide (EDC; concentration: 10 mg/ml) and 10 μl of MES (pH 5.5) were added into 10 μl of a solution of mouse monoclonal anti-TNF-α immunoglobulin G (IgG) (concentration: 0.1 μg/μl; hereinafter as anti-TNF-α) to activate the carboxyl group of anti-TNF-α. After the reaction was performed for 15 minutes at 25° C., the labeling particle and the activated anti-TNF-α were mixed and incubated in PBST overnight at 4° C. Next, the excess antibody were removed by a molecular sieve, and 1% bovine serum albumin (BSA) was added to avoid non-specific binding. Then, the compound of the labeling particle binding with the anti-TNF-α was washed by PBST, and 10 μl of TNF-α protein (product NO. ab9642, provided by Abcam) was added into the compound and the reaction was performed for 1 hour at 25° C., thereby forming the reaction solution including the first complex.

Preparing the Second Complex of the Control Group

Before the second complex was prepared, the binding ligand was modified on each gold nanoparticle. The binding ligand of Example 1 was rabbit polyclonal anti-TNF-α IgG (product NO. ab9635, provided by Abcam), and each of the gold nanoparticles had an equivalent particle size of 80 nm. The following modification method was performed by using Gold Conjugation Kit (product NO. ab154876) produced by Abcam. Specifically, the polyclonal antibody was diluted to a concentration of 0.1 mg/ml, 12 μl of the diluted polyclonal antibody was added into 42 μl of a gold reaction buffer, and the solution was thoroughly mixed. Next, 45 μl of the mixed solution was added into the gold nanoparticles and was uniformly mixed to react for 20 minutes. Then, 5 μl of gold quencher was added, thereby forming the gold nanoparticles modified by the polyclonal antibody. The gold nanoparticles were used to prepare the second complex and the third complex.

6 μl of the gold nanoparticles (modified by the polyclonal antibody) and an analyte standard (TNF-α protein) were simultaneously added into 4 μl of the reaction solution of the first complex, and the reaction was performed for 1 hour at 25° C., thereby forming the second complex, in which the final concentration of the gold nanoparticles was 7.5 OD, and the final concentration of TNF-α protein was 10 μg/ml.

Preparing the Third Complex

The preparation method of the third complex was same as that of the second complex, and there were four groups of the third complexes which respectively had TNF-α protein with different final concentrations in Example 1. The analyte standard of the second complex was replaced into a sample containing the analyte sample (TNF-α protein) in the preparation method of the third complex of Example 1. The sample of Example 1 of the present invention was a diluted analyte standard solution or a solution having higher analyte standard concentration. In the example, the final concentration of the gold nanoparticles in the reaction solution containing the third complex was 7.5 OD, and the final concentrations of the four samples of TNF-α protein were respectively 1, 100, 2 and 50 μg/ml.

Detecting the Heat Diffusivities of the Second Complex and the Third Complex

Figure 4:
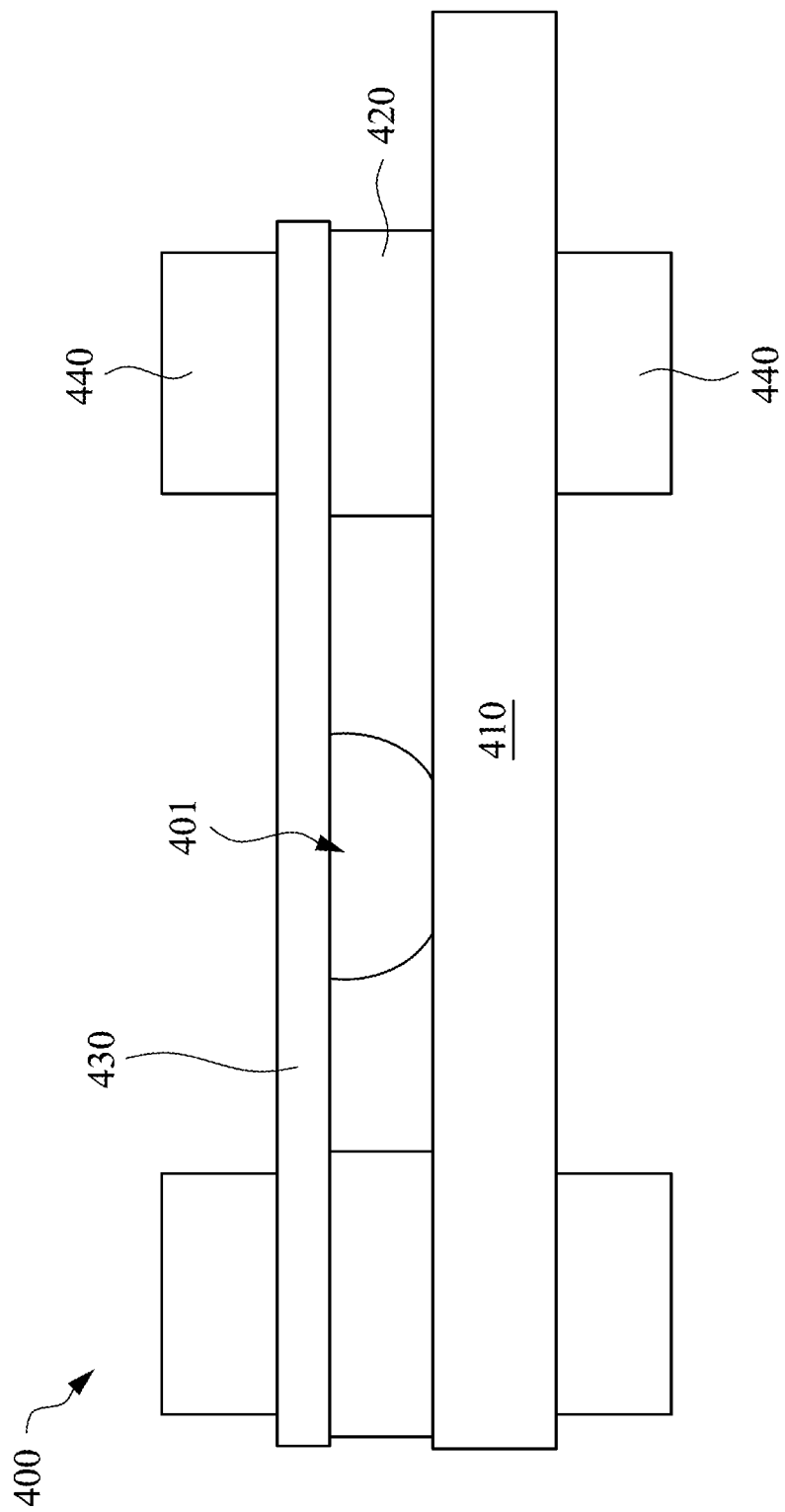
FIG. 4 is a cross-sectional view of a loading device of a sample containing a second complex or a third complex.

FIG. 4 is incorporated to describe the method for detecting the heat diffusivities of the second complex and the third complex. FIG. 4 is a cross-sectional view of a loading device 400 of a sample containing a second complex or a third complex. As shown in FIG. 4, a sample 401 containing the second complex (or the third complex) was loaded on the microscope slide 410. Spacers 420 were disposed on two ends of the microscope slide 410 to provide a loading space for the sample 401. Another microscope slide 430 was disposed on the spacer 420 to cover the sample 401. Magnets 440 were respectively disposed on the outward sides of each microscope slides 410 and 430, so as to fix the loading device 400.

Next, the sample 401 in the loading device 400 was exposed to a mercury light (model: U-RFL-T, provided by Olympus), and a green light laser with a wavelength of 532 nm and a power of 0.23 mW was applied to the sample 401 at the same time. An image overlapping and a cross correlation analysis were performed by using an upright microscope, a camera (FL3-U3-13S2C-CS, provided by Point Grey) and a computer, thereby obtaining an intensity peak of the images, in which the images were captured at a rate of 15 frames/sec for 40 frames/sec. The intensity peak was related to displacements of the second complex and the third complex resulted from Brownian motion per unit time, in which the displacements were calculated by software named Evaluation software for Digital Particle Image Velocimetry (EDPIV). The displacements represented the so-called heat diffusivity of the present invention. A result of Example 1 was shown in FIG. 5A and FIG. 5B. Taiwan Application Serial Number 201725375 was incorporated as a reference to further describe the specific calculation method of the heat diffusivity of the present invention.

EXAMPLES 2-3 AND COMPARATIVE EXAMPLES 1-3

Examples 2-3 and Comparative Examples 1-3 were performed by the same method of Example 1, the difference was that the final concentrations of the analyte standard and/or the analyte sample were changed in Examples 2-3 and Comparative Examples 1-3, so as to examine the detection sensitivity and the detection limit of the method for detecting the analyte concentration. Specific process conditions were listed as Table 1, and may not be repeated herein. A result of Example 2 was shown in FIG. 5C and FIG. 5D, and a result of Example 3 was shown in FIG. 5E and FIG. 5F. Results of Comparative Examples 1-3 were respectively shown in FIG. 6A-FIG. 6C.

EXAMPLE 4

A second complex was used individually to examine the effect on the heat diffusivity by applying the laser in Example 4. The second complex of TNF-α protein having a concentration of 1 μg/ml was used to perform the examination in Example 4, in which the preparation method of Example 4 was performed in a same way as Example 1, and may not be repeated herein. Then, the method for detecting the heat diffusivity of the second complex in Example 1 was applied to examine the heat diffusivity difference with or without the laser applied. A result of Example 4 was shown in FIG. 7A.

EXAMPLE 5

Example 5 was performed in a same way as Example 4. The difference was that the second complex in Example 2

(the concentration of TNF-α protein was 1 ng/ml) was used in Example 5. A result of Example 5 was shown in FIG. 7A.

EXAMPLE 6

Example 6 was performed in a same way as Example 4. The difference was that the second complex in Example 3 was used in Example 6, but the equivalent particle size of each of the gold nanoparticles was 40 nm. A result of Example 6 was shown in FIG. 7B.

EXAMPLE 7

Example 7 was performed in a same way as Example 1. The difference was that the concentration of TNF-α protein of the analyte standard in Example 7 was 10 pg/ml, and the analyte samples of Example 7 were 12.5 µl of tear samples of three subjects. A result of Example 7 was shown in FIG. 8.

EXAMPLE 8

Figure 9A:
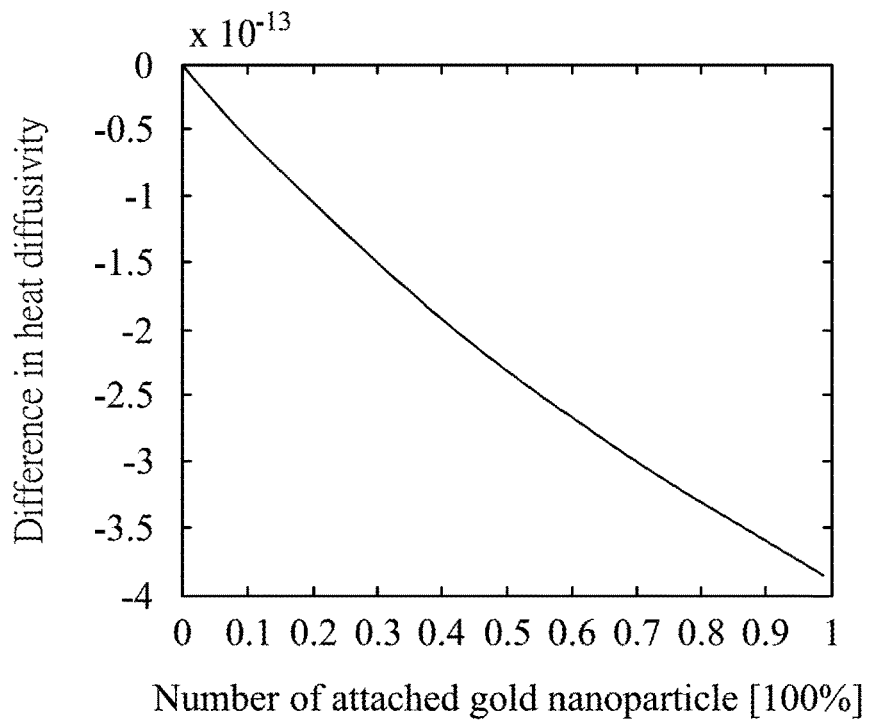
FIG. 9A-FIG. 9D are computer simulation results of Examples 8-11 of the present invention.

A computer software simulation was performed in Example 8 to simulate variation of the heat diffusivity of the second complex with different numbers of the gold nanoparticles binding thereto, in which the second complex was formed by a 100 nm labeling particle (a polystyrene fluorescent particle) and 40 nm gold nanoparticles. The simulation was calculated according to the following mathematical formulas, and it was briefly described as follows: first, the number of the gold nanoparticles binding to the labeling particle was calculated by the formula (1); next, a volume of the labeling particle binding with the gold nanoparticles (i.e. the second complex) was calculated by the formula (2); then, an equivalent particle size of the second complex was calculated by formula (3); afterwards, the heat diffusivity of the second complex at room temperature was calculated by the formula (4). A simulation result of Example 8 was shown in FIG. 9A.

$$N = \frac{4\pi R^2}{\pi r^2} \quad (1)$$

$$V = \frac{4}{3}\pi R^3 + N\frac{4}{3}\pi r^3 \quad (2)$$

$$d_p = \sqrt[3]{\frac{6V}{\pi}} \quad (3)$$

$$D = \frac{K_b T}{3\pi v d_p} \quad (4)$$

in the formulas (1)-(4), R represented the radius of the labeling particle, r represented the radius of each of the gold nanoparticles, N represented the number of the gold nanoparticles binding to a single labeling particle, V represented the volume of the second complex, $d_p$ represented an effective radius, $K_b$ represented Boltzmann constant, v represented viscosity of water, and T represented the temperature (25° C. herein).

EXAMPLES 9-11

Figure 9B:
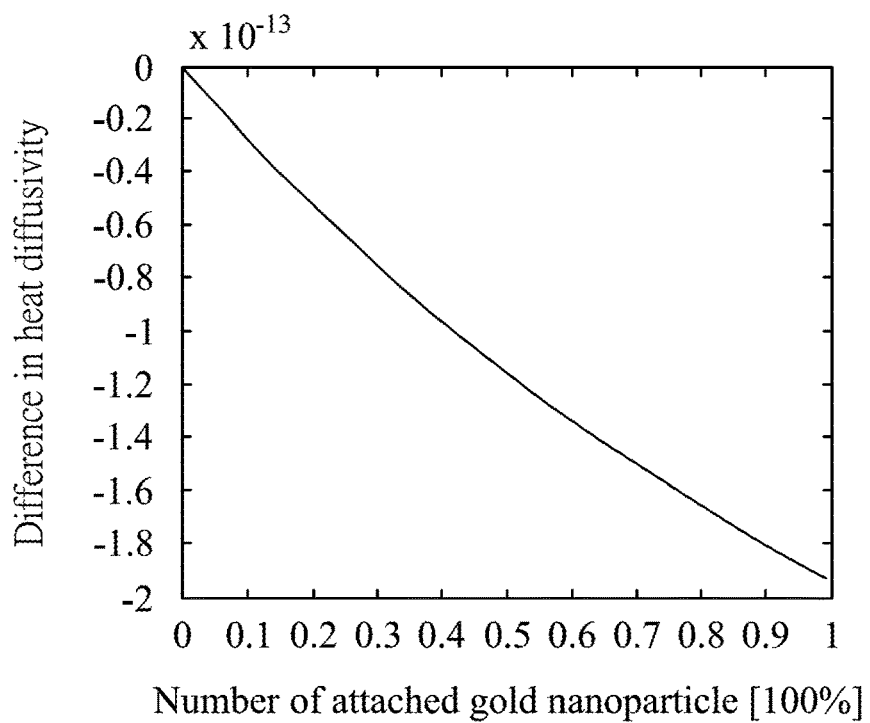
Figure 9C:
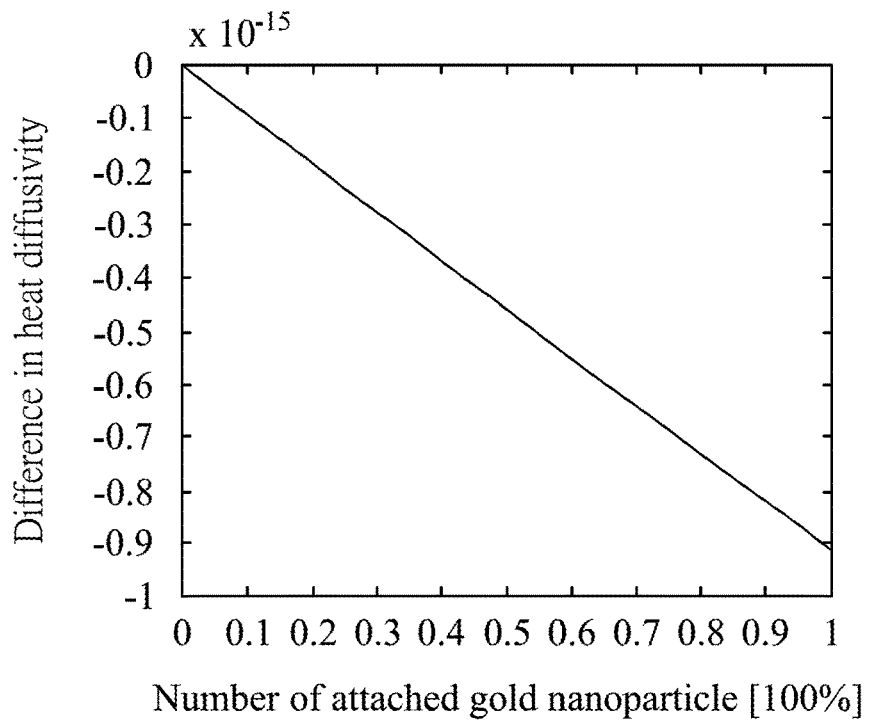
Figure 9D:
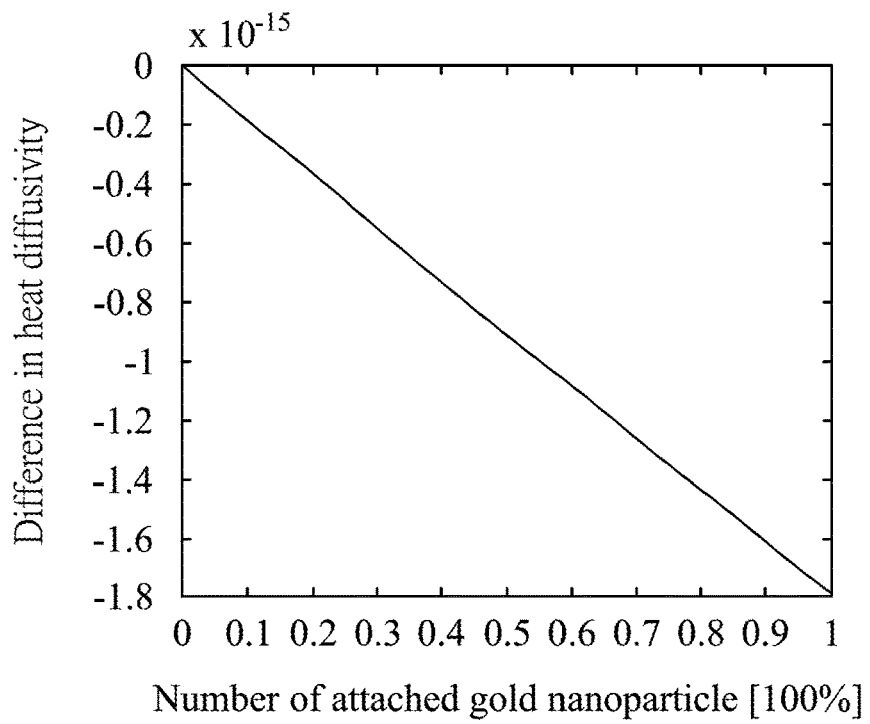

Examples 9-11 were performed in a same way as Example 8. The difference was that the equivalent particle sizes of the labeling particles and/or the gold nanoparticles in Examples 9-11 were changed, in which a 200 nm labeling particle and 80 nm gold nanoparticles were used in Example 9, a 5 µm labeling particle and 40 nm gold nanoparticles were used in Example 10, and a 5 µm labeling particle and 80 nm gold nanoparticles were used in Example 11. Results of Examples 9-11 were shown in FIG. 9B-FIG. 9D.

COMPARATIVE EXAMPLE 4

Comparative Example 4 was performed in a same way as Example 4, but the first complex of Example 1 was used to examine the effect on the heat diffusivity with or without the laser applied in Comparative Example 4. A result of Comparative Example 4 was shown in FIG. 7B.

It is noted that, in FIG. 5A-FIG. 7B of the present invention, "*" represents $p<0.05$, "" represents $p<0.01$, and "*" represents $p<0.001$.

Figure 5A:
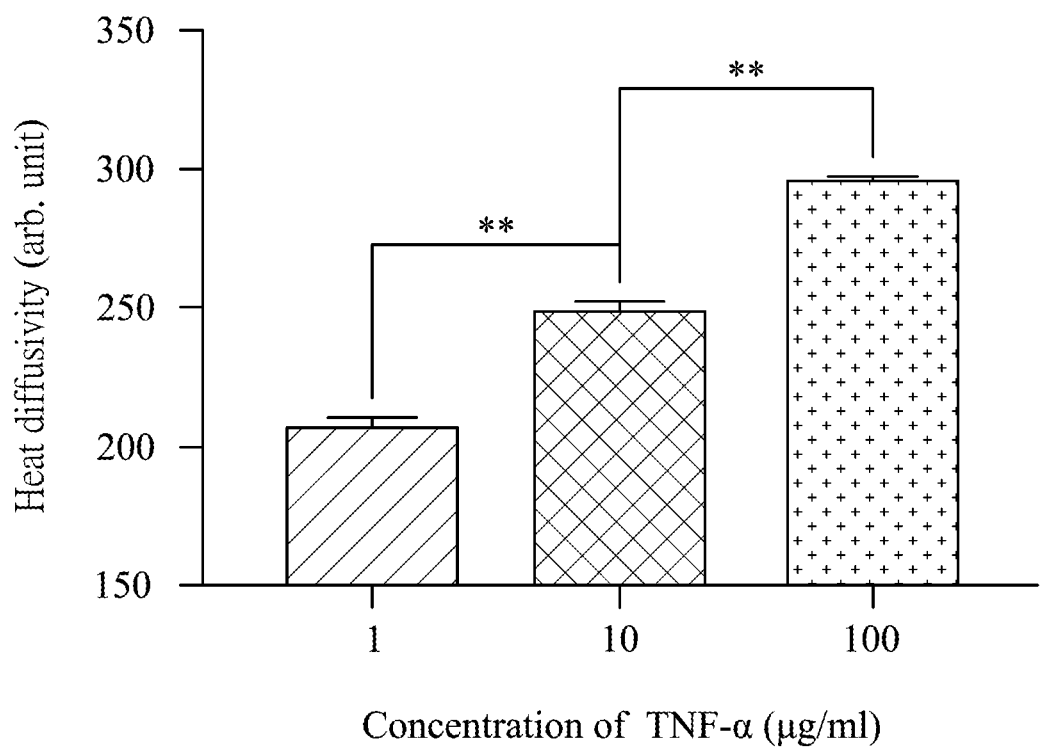
FIG. 5A and FIG. 5B are bar charts of a result for heat diffusivities detected in Example 1 of the present invention.
Figure 5B:
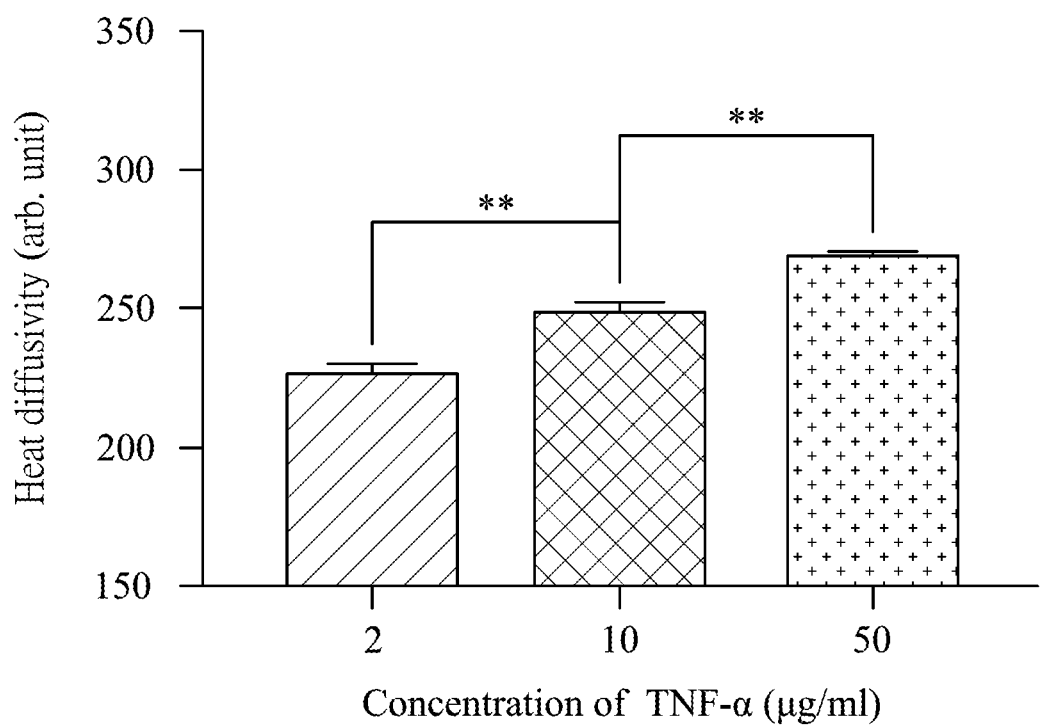
Figure 5C:
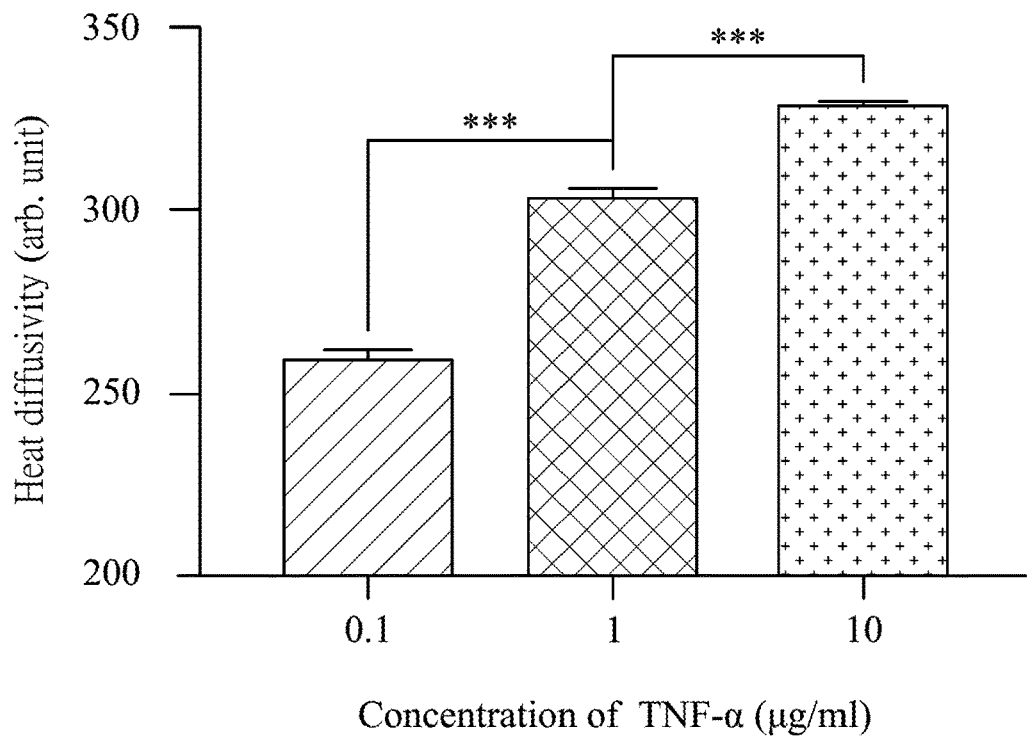
FIG. 5C and FIG. 5D are bar charts of a result for heat diffusivities detected in Example 2 of the present invention.
Figure 5D:
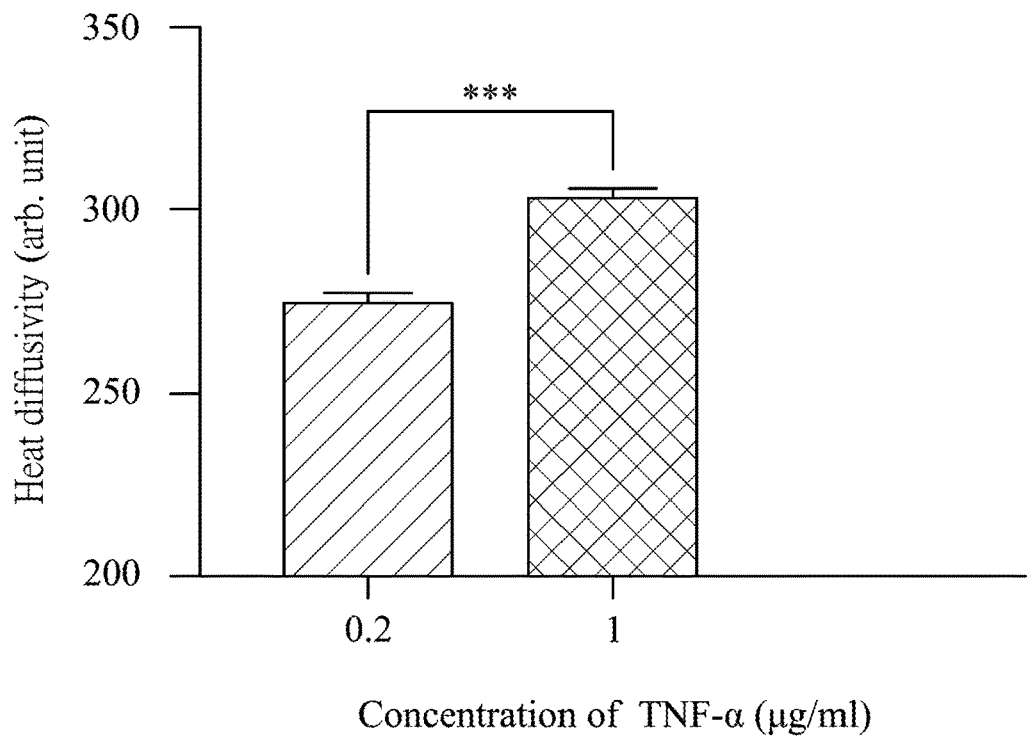
Figure 5E:
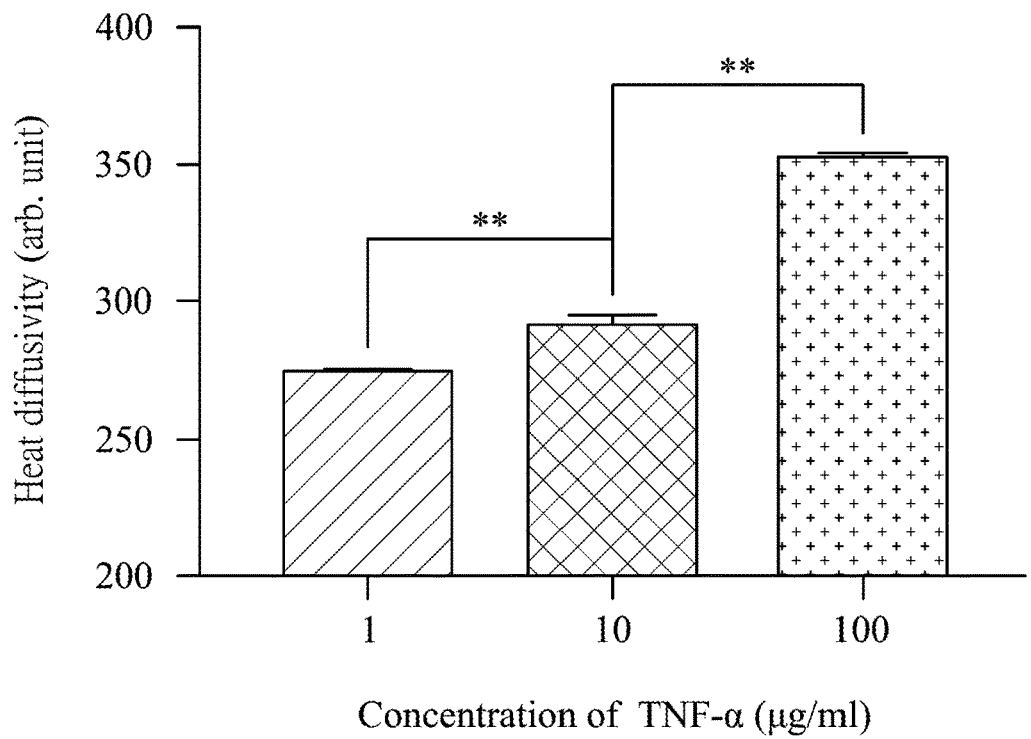
FIG. 5E and FIG. 5F are bar charts of a result for heat diffusivities detected in Example 3 of the present invention.
Figure 5F:
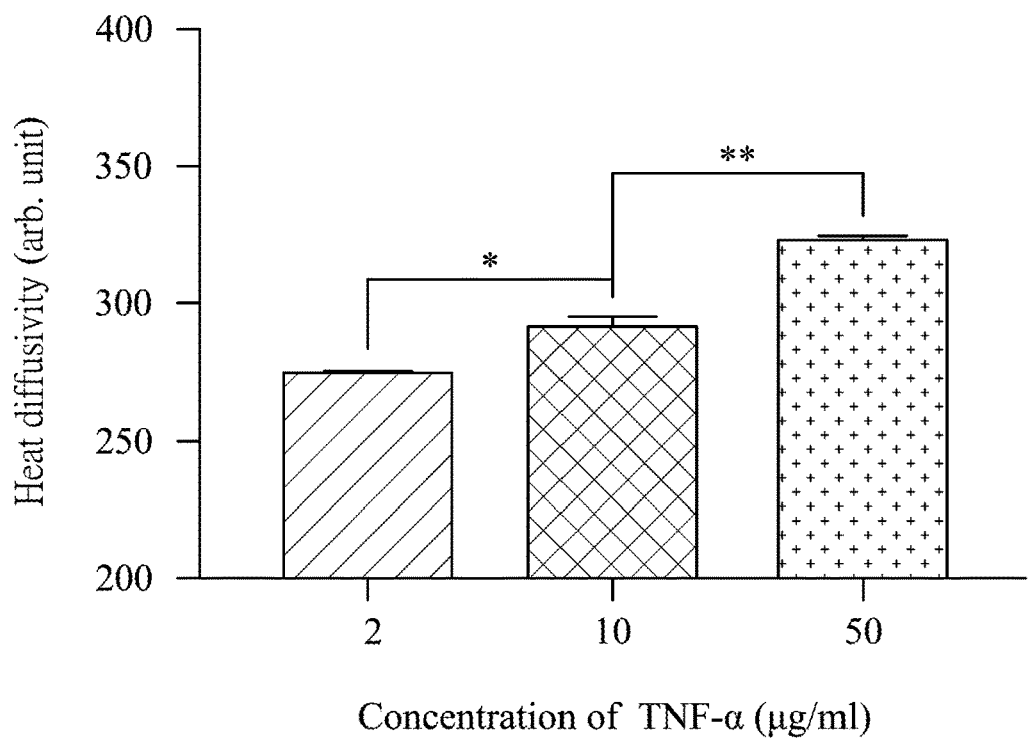

Referring to FIG. 5A-FIG. 5F, FIG. 5A-FIG. 5F are bar charts of a result for the heat diffusivities detected in Examples 1-3 of the present invention. As shown in the figures, the concentrations of the analyte standard TNF-α protein were respectively 10 µg/ml, 1 ng/ml and 10 pg/ml, and the analyte standard could be used to detect the sample having 5-10 times difference in the concentrations from the analyte standard (e.g. FIG. 5A illustrated an example of detecting the analyte sample having 10 times difference in the concentrations (1 µg/ml and 100 µg/ml) from the analyte standard (10 µg/ml)). In the example, the heat diffusivities of the analyte standard and the analyte sample were significantly different. Apparently, the detection limit equal to or greater than 10 pg/ml and a wider dynamic range could be reached by the method of the present invention.

Figure 6A:
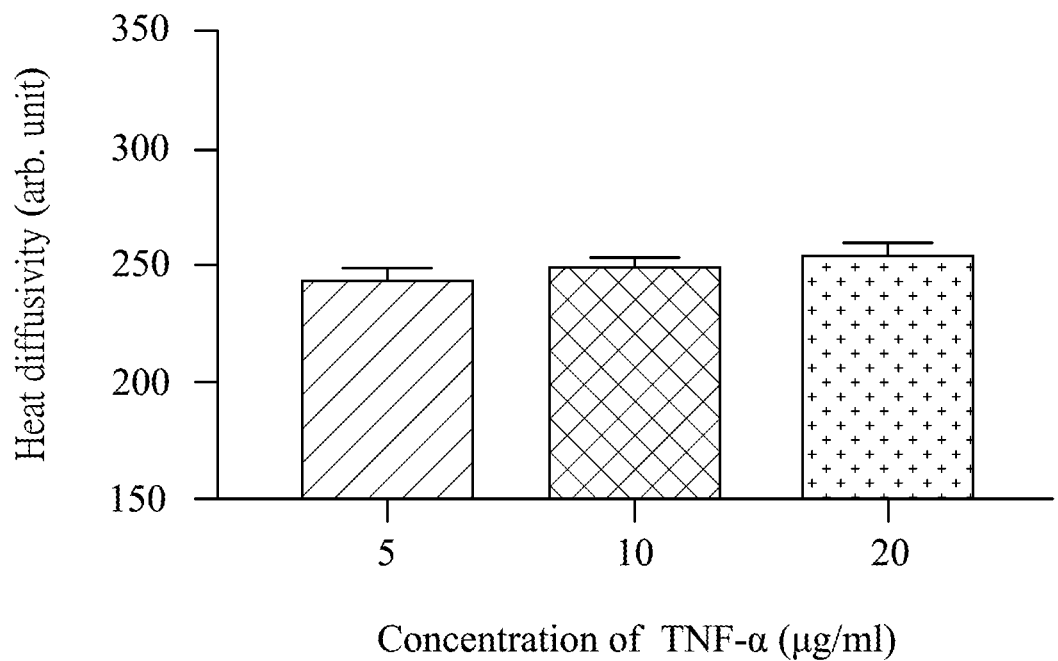
FIG. 6A-FIG. 6C are bar charts of a result for heat diffusivities detected in Comparative Examples 1-3 of the present invention.
Figure 6B:
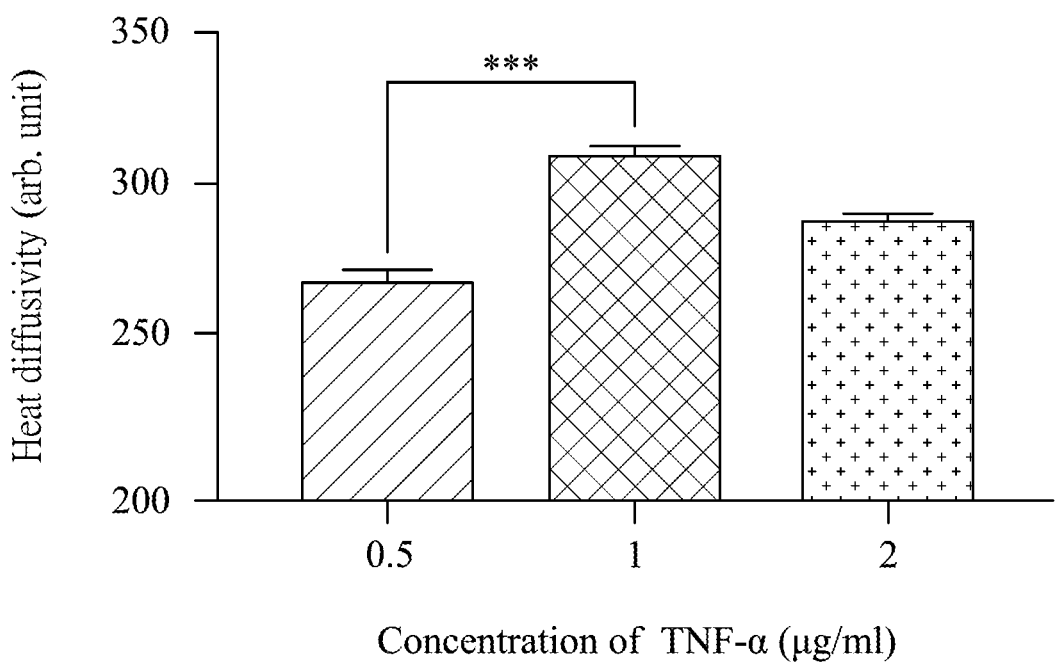
Figure 6C:
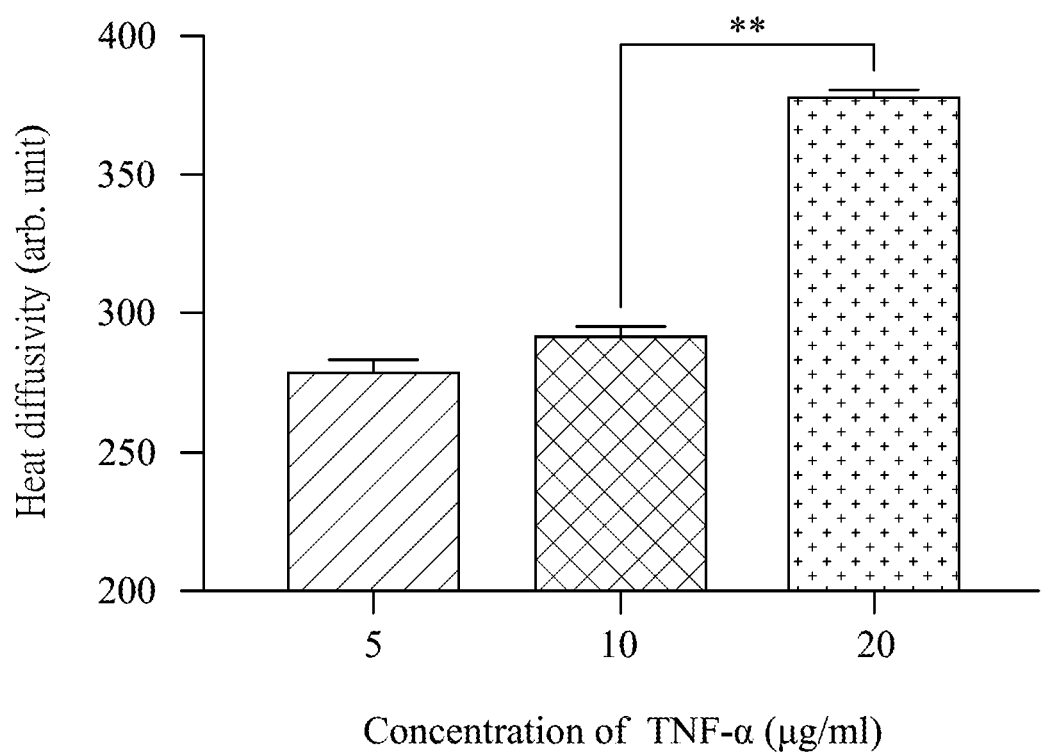

On the other hand, referring to FIG. 6A-FIG. 6C, FIG. 6A-FIG. 6C are bar charts of a result for the heat diffusivities detected in Comparative Examples 1-3 of the present invention. As shown in the figures, the concentrations of the analyte standards are respectively 10 µg/ml, 1 ng/ml and 10 pg/ml in Comparative Examples 1-3. However, when the analyte standard and the analyte sample only have two times difference in the concentrations, the results are not stable. Therefore, it's preferable to apply the method of the present invention when the analyte standard and the analyte sample had the difference in the concentration that was greater than two times.

Figure 7A:
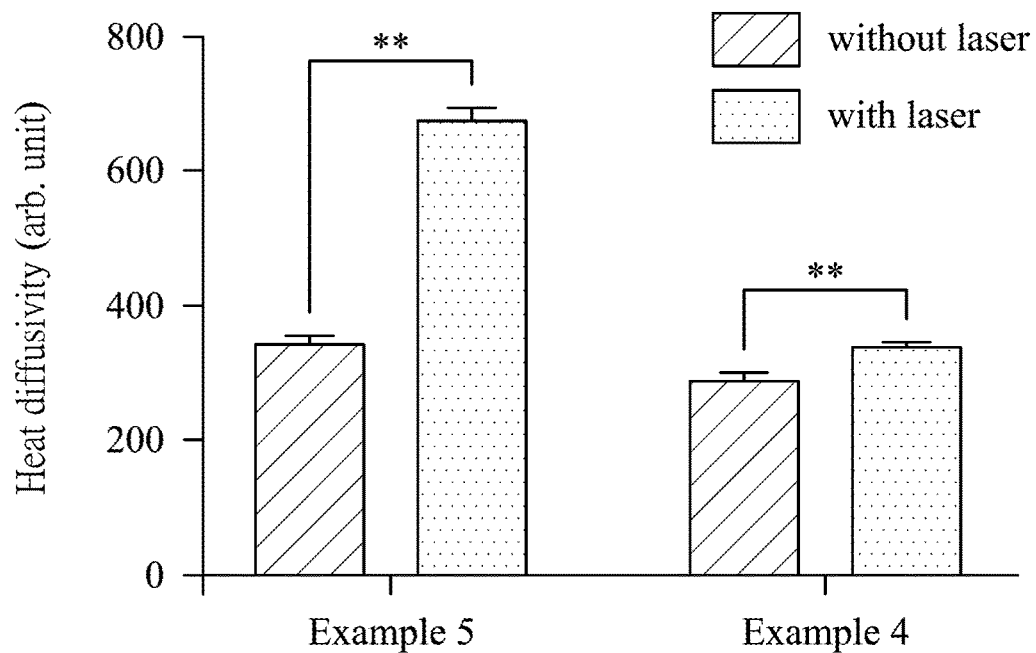
FIG. 7A is a bar chart of a result for heat diffusivities of second complexes detected in Examples 4 and 5 of the present invention with or without a laser applied.

Referring to FIG. 7A, FIG. 7A is a bar chart of a result for the heat diffusivities of the second complexes of Examples 4 and 5 of the present invention with or without a laser applied. As shown in FIG. 7A, the heat diffusivities of the second complexes of Example 4 (the concentration of TNF-α protein was 1 µg/ml) and Example 5 (the concentration of TNF-α protein was 1 ng/ml) both significantly increased, which represented that the vibration of the complex having the gold nanoparticles (the equivalent particle size of 80 nm) might increase after the laser was applied, and thus the sensitivity of the method for detecting the analyte concentration of the present invention could be improved.

Figure 7B:
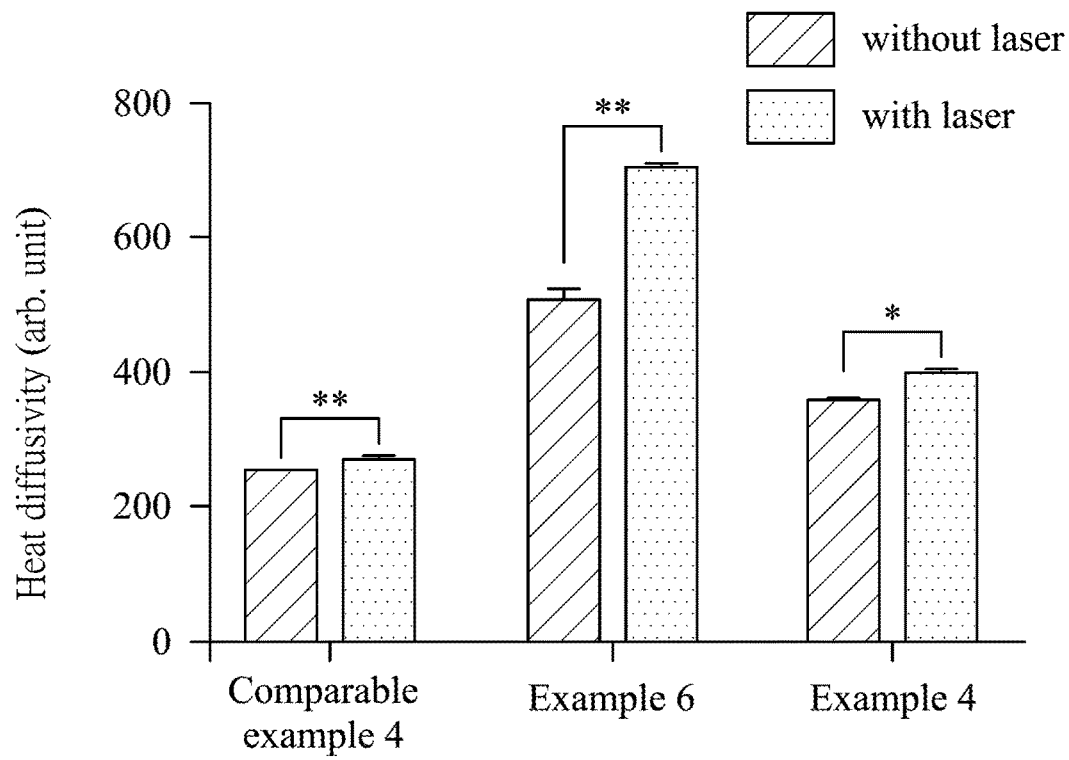
FIG. 7B is a bar chart of a result for heat diffusivities of complexes detected in Examples 4, 6 and Comparative Example 4 of the present invention with or without a laser applied.

Referring to FIG. 7B, FIG. 7B is a bar chart of a result for the heat diffusivities of the complexes of Examples 4, 6 and Comparative Example 4 of the present invention with or without a laser applied. As shown in FIG. 7B, the heat diffusivity of the second complex with the 40 nm gold nanoparticles (Example 6) had significant difference after the laser was applied, compared to the heat diffusivity before the laser was applied. It's because the 40 nm gold nanoparticles matched the wavelength of applied laser and the surface plasmon resonance might occur. The heat diffusivity of the second complex with the 80 nm gold nanoparticles in Example 4 had less significant difference while the difference still existed after the laser was applied, compared to the heat diffusivity before the laser was applied. On the other hand, the heat diffusivity of the first complex without the gold nanoparticles of Comparative Example 4 had statically significant difference after the laser applied, however, it's because the applied laser caused a thermophoresis effect. In addition, the heat diffusivity difference of the first complex without the gold nanoparticles of Comparative Example 4 caused by the applied laser was less significant, compared to that of the second complex with the 40 nm gold nanoparticles.

Figure 8:
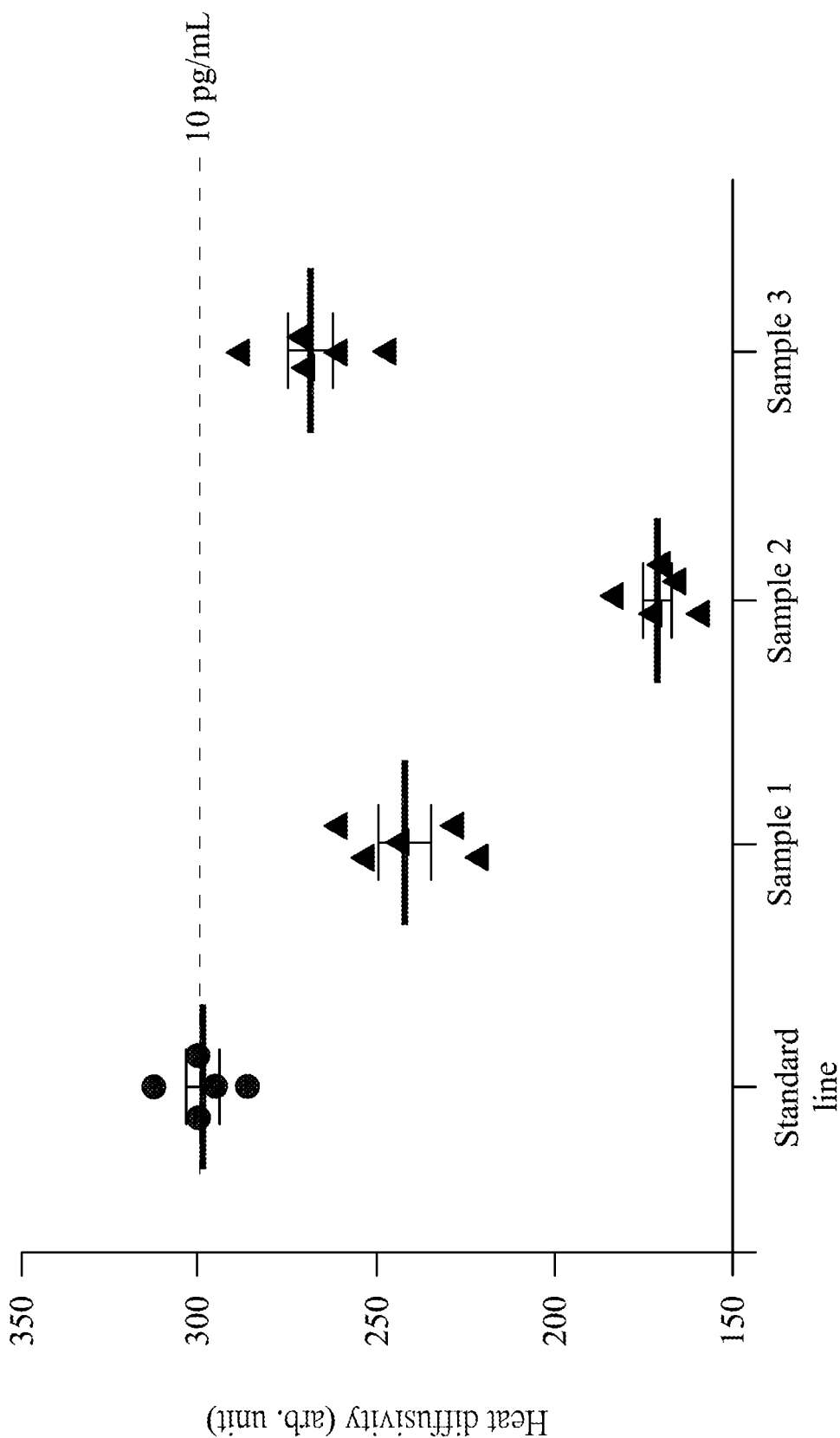
FIG. 8 is an experimental result of applying the method for detecting the analyte concentration to tear sample.

Referring to FIG. 8, FIG. 8 is an experimental result of applying the method for detecting analyte concentration to tear sample. As shown in FIG. 8, the standard line (10 pg/ml) was defined, so as to determine whether the concentration of the specific substance in the sample was higher or lower than the standard line base on the dichotomy method. Therefore, the concentrations of the three samples in FIG. 8 (each sample was performed by 5 times) were lower than the standard line. Accordingly, the method of the present invention was applicable to clinically quick disease screening.

Referring to FIG. 9A-FIG. 9D, FIG. 9A-FIG. 9D are computer simulation results of Examples 8-11 of the present invention. As shown in the figures, the second complex might have different heat diffusivities corresponding to different numbers of the gold nanoparticles binding thereto, in which the second complex was formed by binding the gold nanoparticles not greater than 80 nm with the labeling particle equal to or greater than 100 nm (e.g. 100 nm-5 μm) together. In addition, the overall resolution might reach $10^{-16}$ by using a 100× objective lens with a CCD resolution of 10 μm/pix. Therefore, the heat diffusivities in FIG. 9A-FIG. 9D could be observed by common equipment. Accordingly, at least the labeling particle with a 100 nm-5 μm equivalent particle size and the gold nanoparticles with the equivalent particle size not more than 80 nm might be applicable to the method of the present invention.

In the method for detecting the analyte concentration of the present invention, the analyte standard of the control group and the analyte sample of the sample group are formed by the competition reaction. The heat diffusivity difference of the two groups is examined using the dichotomy method, so as to determine whether the concentration of the analyte sample is higher or lower than the analyte standard, and thus the method has lower detection limit. The metal nanoparticles increase the heat diffusivity difference of the complexes, and the laser is further applied to the metal nanoparticles to cause the surface plasmon resonance. Therefore, the detection sensitivity of the method of the present invention is improved. In addition, the equivalent particle size of the labeling particle has less limitation, and the analyte standard of the present invention may be repeatedly used to perform several groups of detection simultaneously. The method of the present invention has advantages such as high detection sensitivity, a low detection limit, a wide dynamic range, being easy to operate, rapidness, good reproducibility, and low costs. And the method is suitable for the non-invasive disease screening.

Although the present invention has been described in considerable detail with reference to certain embodiments thereof, other embodiments are possible. Therefore, the spirit and scope of the appended claims should not be limited to the description of the embodiments contained herein.

TABLE 1

| | | Example 1 | Example 2 | Example 3 | Comparative Example 1 | Comparative Example 2 | Comparative Example 3 |
|---|---|---|---|---|---|---|---|
| First complex | The equivalent particle size of the labeling particle (nm) | 200 | 200 | 200 | 200 | 200 | 200 |
| | Substrate (TNF-α) concentration (μg/ml) | $10^3$ | 1 | $10^{-2}$ | $10^4$ | 1 | $10^{-2}$ |
| Second complex | The equivalent particle size of the gold nanoparticles (nm) | 80 | 80 | 80 | 80 | 80 | 80 |
| | analyte standard (TNF-α) concentration (μg/ml) | 10 | $10^{-3}$ | $10^{-5}$ | 10 | $10^{-3}$ | $10^{-5}$ |
| Third complex | The equivalent particle size of the gold nanoparticles (nm) | 80 80 80 | 80 80 80 | 80 80 80 | 80 80 80 | 80 80 80 | 80 80 80 |
| | analyte sample (TNF-α) concentration (μg/ml) | 1 100 | 2 50 | $10^{-4}$ $10^{-2}$ $2\times10^{-4}$ | $10^{-6}$ $10^{-4}$ $2\times10^{-6}$ $5\times10^{-5}$ | 5 20 | $5\times10^{-4}$ $2\times10^{-3}$ $5\times10^{-6}$ $2\times10^{-5}$ |
| Whether applying the green light laser or not | | ○ | ○ | ○ | ○ | ○ | ○ |
| A ratio of the equivalent particle sizes of the labeling particle to the gold nanoparticles | | 2.5 | 2.5 | 2.5 | 2.5 | 2.5 | 2.5 |

What is claimed is:

1. A method for detecting an analyte concentration, comprising:
providing at least two reaction solutions, wherein each of the reaction solutions comprises a first complex, and the first complex comprises:
a labeling particle;
a binding ligand, fixed on a surface of the labeling particle;
and
a substrate, binding to the binding ligand;

simultaneously adding an analyte standard and metal nanoparticles into one of the reaction solutions, so as to form a second complex, wherein the binding ligand is modified onto each of the metal nanoparticles, the substrate of the first complex binds to the binding ligand of the metal nanoparticles for forming the second complex, and the analyte standard in the one of the reaction solutions has a known concentration;

simultaneously adding a sample including an analyte sample and the metal nanoparticles into the other one of the reaction solutions, so that the substrate of the first complex binds the binding ligand of the metal nanoparticles to form a third complex, wherein the analyte sample in the other reaction solution has an unknown concentration, an equivalent particle size of the labeling particle is greater than an equivalent particle size of each of the metal nanoparticles, and the substrate, the analyte standard and the analyte sample are substantially the same substance; and detecting a first heat diffusivity of the second complex and a second heat diffusivity of the third complex using a light source; and performing an analyte concentration determination step, wherein when the first heat diffusivity is less than the second heat diffusivity, the unknown concentration is higher than the known concentration; or, when the first heat diffusivity is greater than the second heat diffusivity, the unknown concentration is lower than the known concentration.

2. The method of claim 1, wherein detecting the first heat diffusivity and the second heat diffusivity using the light source further comprises applying a laser to the metal nanoparticles.

3. The method of claim 1, wherein the equivalent particle size of each of the metal nanoparticles is not greater than 80 nanometers (nm).

4. The method of claim 1, wherein an equivalent particle size of the labeling particle is equal to or greater than 100 nm.

5. The method of claim 4, wherein a ratio of the equivalent particle sizes of the labeling particle to one of the metal nanoparticles is 2.5 to 125.

6. The method of claim 1, wherein a material of the metal nanoparticles comprises gold.

7. The method of claim 1, wherein a material of the labeling particle comprises a fluorescent compound.

8. The method of claim 2, wherein a power of the laser is not greater than 0.23 mW.

9. The method of claim 1, wherein the sample comprises tear, blood, urine or serum.

10. The method of claim 1, wherein the unknown concentration is equal to or greater than 10 pg/ml.

11. The method of claim 1, wherein the light source excites the respective labeling particles of the second complex and the third complex.

12. The method of claim 1, wherein the light source comprises a mercury lamp, a xenon lamp, or a metal halide lamp.

13. The method of claim 1, wherein the binding ligand comprises an antigen, an antibody, a receptor or a ligand.

14. The method of claim 13, wherein the substrate, the analyte standard and the analyte sample respectively comprise an antibody of the antigen of the binding ligand, an antigen of the antibody of the binding ligand, a ligand of the receptor of the binding ligand, or a receptor of the ligand of the binding ligand.

* * * * *